United States Patent [19]

Sabourin et al.

[11] 4,158,090

[45] Jun. 12, 1979

[54] EPOXY RESIN COMPOSITIONS (CASE B) CONTAINING CUMENE-MALEIC ANHYDRIDE RESIDUE

[75] Inventors: Edward T. Sabourin, Allison Park; Walter P. Barie, Jr., Glenshaw, both of Pa.

[73] Assignee: Gulf Research & Development Company, Pittsburgh, Pa.

[21] Appl. No.: 879,446

[22] Filed: Feb. 21, 1978

[51] Int. Cl.² ............... C08G 59/16; C08G 59/18; C08G 59/68

[52] U.S. Cl. ............... 528/92; 260/346.74; 264/331; 528/93; 528/112; 528/365

[58] Field of Search ............... 260/346.74, 47 EC; 528/92, 93, 112, 365

[56] References Cited

U.S. PATENT DOCUMENTS

| | | | |
|---|---|---|---|
| 2,692,270 | 10/1954 | Beavers | 260/346.74 |
| 3,297,723 | 1/1967 | Selwitz | 260/347.3 |
| 3,409,638 | 11/1968 | Selwitz | 260/346.74 |
| 3,523,143 | 8/1970 | Kwong | 260/47 EC |
| 3,709,840 | 1/1973 | Dehoff | 260/47 EC |

OTHER PUBLICATIONS

Handbook of Epoxy Resins, Lee et al., 11-10, 11-11, 1968.

Primary Examiner—Howard E. Schain

[57] ABSTRACT

A new composition capable of being cured to a solid resin highly resistant to boiling acetone which comprises: (a) a 1,2-epoxy resin containing on the average more than one 1,2-epoxy group per molecule; (b) a residue remaining from the process wherein cumene (C) is reacted with maleic anhydride (MA) in the presence of (that is, in contact with) zinc chloride to obtain a reaction product containing dimethylbenzyl succinic anhydride (DMBSA), 5-phenyl-5-methylhexane-1,2,3,4-tetracarboxylic acid dianhydride (PMTD) and addition products of C and MA containing more than two anhydride groups per molecule (AP) and wherein a sufficient amount of said DMBSA is removed from said reaction product to give a residue containing a maximum of 25 weight percent DMBSA; and (c) an accelerator.

15 Claims, No Drawings

EPOXY RESIN COMPOSITIONS (CASE B) CONTAINING CUMENE-MALEIC ANHYDRIDE RESIDUE

BACKGROUND OF THE INVENTION

1. Field of the Invention

This invention relates to new and useful epoxy resin compositions, especially those capable of being cured to solid resins which are highly resistant to boiling acetone and are lighter in color. Epoxy resins are well-known in the art and comprise a molecule which contains on the average more than one epoxy group. The resins are converted into hard, infusible cross-linked polymers by curing. Curing of the resins can be effected, for example, by a catalytic polymerization process or by a coupling process. The compositions of the present invention are formed by the coupling process wherein the epoxy resin is reacted with specific poly-functional cross-linking agents to couple or cross-link one epoxy resin molecule with another.

The properties of the epoxy resins and the finished polymers will depend, of course, on the nature of the epoxy resin and the cross-linking agents. For some applications, for example, encapsulation and bonding, it is desirable that molded products and powder coatings be highly resistant to chemicals and solvents, especially boiling acetone (U.S. Pat. No. 3,324,081) and that epoxy compositions be light in color. To supply this need, the present invention herein provides a new composition capable of being cured to a solid highly resistant to boiling acetone which comprises (a) a 1,2-epoxy resin containing on the average more than one 1,2-epoxy group per molecule; (b) a residue remaining from the process wherein cumene (C) is reacted with maleic anhydride (MA) in the presence of (that is, in contact with) zinc chloride to obtain a reaction product containing dimethylbenzyl succinic anhydride (DMBSA), 5-phenyl-5-methylhexane-1,2,3,4-tetracarboxylic acid dianhydride (PMTD) and addition products of C and MA containing more than two anhydride groups per molecule (AP) and wherein a sufficient amount of said DMBSA is removed from said reaction product to give a residue containing a maximum of 25 weight percent DMBSA; and (c) an accelerator.

2. Description of the Prior Art

Applicant is unaware of any prior art relevant to the invention defined and claimed herein.

SUMMARY OF THE INVENTION

We have discovered a new composition capable of being cured to a solid resin highly resistant to boiling acetone which comprises:

(a) a 1,2-epoxy resin containing on the average more than one 1,2-epoxy group per molecule;

(b) a residue remaining from the process wherein cumene is reacted with maleic anhydride in the presence of zinc chloride to obtain a reaction product containing dimethylbenzyl succinic anhydride, 5-phenyl-5-methylhexane-1,2,3,4-tetracarboxylic acid dianhydride and addition products of cumene and maleic anhydride containing more than two anhydride groups per molecule and wherein a sufficient amount of said dimethylbenzyl succinic anhydride is removed from said reaction product to give a residue containing a maximum of 25 weight percent dimethylbenzyl succinic anhydride; and (c) an accelerator.

DETAILED DESCRIPTION OF THE COMPOSITION

1,2 Epoxy Resins

The composition contains a 1,2-epoxy resin containing on the average more than one 1,2-epoxy group per molecule. Any of the epoxy resins well known in the art can be employed in the new composition of this invention. By an epoxy resin is meant any molecule which contains on the average more than one epoxy group. An epoxy group is a three-membered ring containing one oxygen and two carbon atoms. Epoxy resins having molecular weights between about 75 and 4000 are known. The more preferred epoxy resins are generally prepared by the reaction of an epihalohydrin with a polyhydric alcohol or phenol. The reaction products are complex mixtures of polyethers having terminal 1,2-epoxide groups and in which alternatng intermediate aliphatic hydroxy-containing radicals are linked through ether oxygens to aliphatic or aromatic nuclei. Other suitable epoxy resins include, for example, butane dioxide and limonene dioxide.

The high molecular weight complex polyether composition are thermoplastic, but are capable of forming thermosetting compositions by further reaction through the hydroxy and/or 1,2-epoxide groups with a cross-linking agent. In order to form these thermosetting compositions, the epoxy resin must have a 1,2-epoxide equivalency greater than one. By epoxide equivalency is meant the average number of 1,2-expoxide groups contained in the measured molecular weight of the resin. Since the epoxy resin is a mixture of polyethers, the measured molecular weight, upon which the 1,2-epoxide equivalency depends, is necessarily an average molecular weight. Hence, the 1,2-epoxide equivalency of the resin will be a number greater than one, but not necessarily an integer. If the measured molecular weight and epoxide value are given, the 1,2-epoxide equivalency can easily be determined. For example, an epoxy resin having an average molecular weight of 900 and an epoxide value of 0.2 has a 1,2-epoxide equivalency of 1.8.

The epoxide value of an epoxy resin is the number of epoxide groups per 100 grams of resin. This value can be determined experimentally by heating a one-gram sample of the epoxy resin with an excess of a pyridine solution of pyridine hydrochloride (obtained by adding sixteen milliliters of concentrated hydrochloric acid to a liter of pyridine) at the boiling point for twenty minutes and then back titrating the unreacted pyridine hydrochloride with 0.1N NaOH to the phenolphthalein end point. In the calculations, each HCl consumed by the resin is considered to be equivalent to one epoxide group.

The preferred epoxy resins are prepared by the reaction of epichlorohydrin with a dihydric phenol and have the general formula:

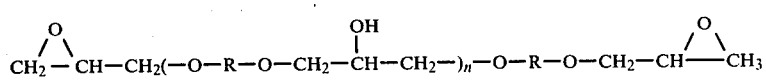

where R is a divalent aromatic radical and n is an integer between 0 and about 18. As the ratio of the epichlorohydrin to dihydric phenol increases, the value of n decreases.

Bisphenol A [bis(4-hydroxy phenyl) dimethyl methane] is perhaps the dihydric phenol most frequently employed. Thus, R is in the above formula would be:

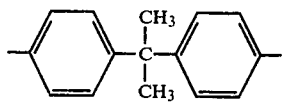

When n in the above formula is zero, a diglycidyl ether having the following formula results:

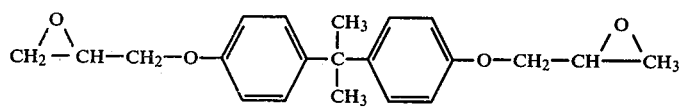

The above ether can be obtained when the mol ratio of epichlorohydrin to Bisphenol A is about 10:1. Lower ratios will produce higher molecular weight polyethers. The epoxide equivalent (which is defined as the weight of resin in grams containing 1 gram equivalent of epoxy) should be between about 400 and 4000, preferably between 500 and 2500, which is one-half the average molecular weight. These epoxy resins are solid at room temperature (20°–25° C.) and have a Durran melting point between about 50° C. and 150° C. Many commercially available epoxy resins with suitable properties may be employed. For example, suitable resins include "Bakelite ERL 2002"; "Bakelite ERL 2003"; "Epon 1001" and "Epon 1004". "Bakelite" is the trademark of Union Carbide Corporation and "Epon" is the trademark of the Shell Chemical Company.

Residue

A residue is formed as a remainder from the process wherein C is reacted with MA in the presence of zinc chloride to obtain a reaction product containing DMBSA, PMTD and AP and wherein a sufficient amount of said DMBSA is removed from said reaction product to give a residue containing a maximum of 25 weight percent DMBSA. If more than 25 percent of DMBSA remains in the residue, the residue becomes gummy and cannot be ground into a free-flowing powder. The reaction of C with MA is well known in the art and is taught, for example in U.S. Pat. Nos. 2,692,270, 3,297,723 and 3,409,638.

A typical preparation of the residue is, in general, as follows. C and MA (in the range of about 0.1 to about 10 moles, preferably about 0.5 to about 5 moles, of C per mole of MA) and anhydrous zinc chloride (about 0.003 to about 0.2 moles, preferably about 0.01 to about 0.05 moles per mole of MA) are charged to a reaction vessel and a nitrogen atmosphere is established at any suitable pressure, preferably atmospheric (ambient) pressure. The reaction mixture is heated to about 125° C. to about 200° C., preferably about 130° C. to about 160° C., at any suitable pressure, preferably atmospheric pressure. Additional molten MA (about 0 to about 5, preferably about 1 to about 3 times the initial charge of MA), C (about 0 to about 10, preferably about 1 to about 5 times the initial charge of C), and an initiator (about 0.1 to about 10, preferably about 1 to about 5 mole percent relative to the total MA) are added over a 1 to 4 hour interval. Any initiator known in the art for the defined reaction can be used, specific examples of which are peroxides, such as benzoyl peroxide, lauryl peroxide, dicumyl peroxide, etc., azo compounds, such as azo-bis-cyclohexylnitrile, etc. are known initiators. An especially preferred initiator is azobisisobutyronitrile. A solvent essentially inert under the reaction conditions, e.g. 5-butylbenzene, chlorobenzene, etc., may be employed, but excess C is generally preferred. Unreacted C and MA are distilled from the mixture under any suitable pressure, for example, atmospheric to about 15 mm pressure. The reaction mixture is allowed to cool to about 100° to about 130° C., preferably about 110° to about 120° C. and the stirring is stopped at which point a red complex containing the zinc chloride settles out of solution. The liquid portion of the reaction mixture is decanted from the zinc chloride complex, preferably through a filter, and placed in a distillation pot. The unreacted C and MA are distilled from the mixture under atmospheric to about 15 mm pressure. The DMBSA (approximately 75 weight percent) is distilled at a temperature ranging from about 130° to about 190° C., preferably about 140° to about 170° C. and at a pressure ranging from about 0.1 to about 4 mm, preferably about 0.1 to about 2 mm. The molten pot residue is discharged and allowed to cool to ambient temperature. The residue after cooling will be a hard, light yellow, translucent material. The residue is ground to a light yellow powder under conditions which restrict excessive contract with moisture in the air, for example, under a blanket of dry nitrogen. The residue will consist essentially of about 5 to about 25 weight percent, preferably about 5 to about 15 weight percent of DMBSA; about 40 to about 90 weight percent, preferably about 50 to about 80 weight percent of PMTD; and about 5 to about 50 weight percent, preferably about 10 to about 40 weight percent AP.

Accelerator

Any accelerator known in the art can be used to speed up the reaction between the 1,2-epoxy resin and the residue. Typical accelerators can include, for example, tin octanoate, zinc acetylacetonate, and benzyldimethylamine. An especially preferred accelerator is tin octanoate.

The 1,2-epoxy resin, residue, and accelerator are mixed, for example, in a ball mill using Burundum balls for 16 to 24 hours at ambient temperature and pressure to obtain a fine powder. The powder ranges in particle size so that substantially all will go through a 50 mesh screen.

The expression A/E ratio is used in the epoxy resin art to indicate the ratio of total anhydride equivalents to total epoxy equivalents in an uncured resin formulation. The cured resin prepared in accordance with this invention from a solid epoxy resin and the residue remaining from the process wherein C is reacted with MA to obtain a reaction product containing DMBSA, PMTD and AP and wherein a sufficient amount of said DMBSA is removed from said reaction product to give a residue containing a maximum of 25 weight percent DMBSA has a broad range of A/E ratio of about 0.95 to about 1.50 and a more preferred range of about 1.0 to about 1.40. The broad range of accelerator is from about 0.1 to about 8.0 parts per hundred parts resin (phr). The more preferred range is from about 1.0 to 4.0 phr.

The curing mechanism of the epoxy resin and an anhydride hardener in the presence of an accelerator is described in Lee and Neville "Handbook of Epoxy Resins" McGraw-Hill Book Company, N.Y., pages 5-20 to 5-26.

DESCRIPTION OF PREFERRED EMBODIMENTS

The invention will be further described with reference to the experimental data.

EXAMPLE 1

A two liter round bottom flask equipped with a magnetic stirrer, heating mantle, thermometer, a nitrogen inlet and outlet, a condenser, and two pressure compensating dropping funnels was charged with 98 grams of MA, 120 gram of C, and 3 gram anhydrous zinc chloride. A nitrogen atmosphere was established, and the temperature was raised to 145° C. One addition funnel, heated by an electric heating tape, contained an additional 98 gram of molten MA which was added dropwise over a two-hour period. Simultaneously, 480 gram of C containing 8 gram of azo-bis-isobutyronitrile was added dropwise over a 2.5-hour period from the other dropping funnel. After the addition was completed, the temperature was maintained for an additional hour. The stirring was then stopped and the mixture allowed to cool to approximately 120° C. whereupon a red complex containing the zinc chloride settled out. The supernatant liquid was decanted into a distillation flask and the unreacted C was removed at atmospheric pressure. After the bulk of the C had distilled, the pressure was reduced to 15 mm Hg to remove traces of unreacted MA along with the remaining C. The pressure was then reduced to about 2 mm Hg. After a small forecut, a cut of pure DMBSA boiling at 155° to 160° C. was taken (170 gram). The molten residue was discharged and allowed to cool to room temperature. The amber glass-like material weighing 121 gram was ground using a Wiley mill in an inert atmosphere to give a free-flowing light yellow powder (100 mesh). This product contained 15 weight percent DMBSA, 76 weight percent PMTD, and 10 weight percent AP.

When the above procedure was followed without use of zinc chloride, a much darker colored material of essentially the same composition was obtained. Because judgment of color of solids can be influenced greatly by slight changes in particle size, the magnitude of color improvement was determined on the crude reaction mixtures just prior to distillation. For this purpose a Klett Colorimeter was employed with a light path of 2 cm and using pure cumene as the reference solution. The sample made by a process which employed zinc chloride gave a reading of 270 whereas the sample made by a process without zinc chloride gave a reading of 620.

Zinc chloride is unique in this procedure since similar runs employing aluminum chloride, stannous chloride, sodium chloride, and zinc oxide failed to give any color improvement.

EXAMPLE 2

Molding Powder Formulation

A powder formulation was prepared from 50.0 grams of Epon 1004, 10.3 gram of the product from Example 1 and 1.0 gram tin octanoate (2 phr). The A/E ratio was 1.0. The A/E ratio is the ratio of total anhydride equivalents to total epoxy equivalents in an uncured resin formulation. The powder was added to a ball mill using Burundum balls for 16 hours. Prior to molding, the powder was passed through a sieve having a 50 mesh screen.

The powder was molded into a disc shape at a temperature of 165° C. and at a pressure of 1600 psi for 30 minutes.

A similar powder formulation using PMTD alone was also made for comparison with the above product. The same A/E ratio, accelerator and molding conditions were also used.

EXAMPLE 3

Boiling Acetone Test

The boiling acetone test involved the heating of the cured epoxy resin sample in boiling acetone for one hour. The samples were accurately weighed before the test and after the test to determine the weight change in deterioration of the sample. Acetone is a very good solvent and the exposure of cured epoxy resins at its boiling point for one hour provided a convenient method to determine completion of cure and cross-linking efficiency.

The results of the boiling acetone resistance test are reported in Table 1.

Table 1:

| Results of Boiling Acetone Resistance Test | |
| --- | --- |
| Run No. | Weight Change after One Hour in Boiling Acetone |
| 1 | 9.8 |
| 2 | 15.2 |

The results in Table 1 compare the acetone resistance of cured epoxy resins prepared using PMTD (Run 1) with those prepared in accordance with the present invention (Run 2). Generally these results show that the cured epoxy resin prepared in accordance with the present invention herein has a lower weight change than that observed for the product using PMTD. These results are unusual since the PMTD residue contains significant quantities of DMBSA, which is a monoanhydride along with the heavier material. The cross-linking density of the epoxy resins cured with monoanhydrides is less than that obtained with di- or polyanhydride; therefore it would be expected that the resulting product would be more susceptible to boiling acetone. However, this was not the case, and it has been demonstrated that the product prepared in accordance with the present invention is more stable to boiling acetone as shown by only 9.8% weight change versus a 15.2% weight change for the PMTD product.

Obviously, many modifications and variations of the invention, as hereinabove set forth, can be made without departing from the spirit and scope thereof, and, therefore, only such limitations should be imposed as are indicated in the appended claims.

We claim:

1. A new composition capable of being cured to a solid resin highly resistant to boiling acetone which comprises:
   (a) a 1,2-epoxy resin containing on the average more than one 1,2-epoxy group per molecule;

(b) a residue remaining from the process wherein cumene is reacted with maleic anhydride in the presence of zinc chloride to obtain a reaction product containing dimethylbenzyl succinic anhydride, 5-phenyl-5-methylhexane-1,2,3,4-tetracarboxylic acid dianhydride and addition products of cumene and maleic anhydride containing more than two anhydride groups per molecule and wherein a sufficient amount of said dimethylbenzyl succinic anhydride is removed from said reaction product to give a residue containing a maximum of 25 weight percent dimethylbenzyl succinic anhydride; and (c) an accelerator.

2. A new composition according to claim 1 wherein said 1,2-epoxy resin has a molecular weight ranging from about 75 to about 4000.

3. A new composition according to claim 1 wherein said 1,2-epoxy resin is prepared by the reaction of an epihalohydrin with a polyhydric alcohol or phenol.

4. A new composition according to claim 1 wherein said 1,2-epoxy resin is prepared by the reaction of epihalohydrin with a dihydric phenol to produce a compound having the general formula:

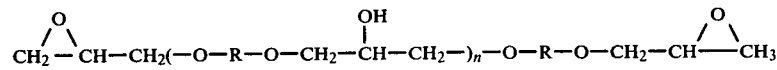

where R is a divalent aromatic radical and n is an integer between 0 and 18.

5. A new composition according to claim 1 wherein said 1,2-epoxy resin has an epoxide equivalent between about 300 and about 4000.

6. A new composition according to claim 1 wherein said 1,2-epoxy resin has an epoxide equivalent between about 400 to about 2500.

7. A new composition according to claim 1 wherein said 1,2-epoxy resin is solid at room temperature (20°–25° C.) and has a Durran melting point between about 50° to about 150° C.

8. A new composition according to claim 1 wherein said residue consists essentially of about 5 to about 25 weight percent of said dimethylbenzyl succinic anhydride, about 40 to about 90 weight percent of said 5-phenyl-5-methylhexane-1,2,3,4-tetracarboxylic acid dianhydride, and about 5 to about 50 weight percent of said addition products.

9. A new composition according to claim 1 wherein said residue consists essentially of about 5 to about 15 weight percent of said dimethylbenzyl succinic anhydride, about 50 to about 80 weight percent of said 5-phenyl-5-methylhexane-1,2,3,4-tetracarboxylic acid dianhydride, and about 10 to about 40 weight percent of said addition products.

10. A new composition according to claim 1 wherein said accelerator is selected from the group consisting of tin octanoate, zinc acetylacetonate, and benzyldimethylamine.

11. A new composition according to claim 1 wherein said accelerator is tin octanoate.

12. A new composition according to claim 1 wherein said cured solid resin has a total anhydride equivalent ratio of about 0.95 to about 1.50 and an amount of said accelerator ranging from about 0.1 to about 8.0 parts per hundred parts resin.

13. A new composition according to claim 1 wherein said cured solid resin has a total anhydride equivalent ratio of about 1.0 to about 1.40 and an amount of said accelerator ranging from about 1.0 to about 4.0 parts per hundred parts resin.

14. A new composition according to claim 1 wherein said 1,2-epoxy resin has an epoxide equivalent between about 300 to about 4,000, is a solid at room temperature (20°–25° C.) and has a Durran melting point between about 50° and 150° C.; said residue consists essentially of about 5 to about 25 weight percent of said dimethylbenzyl succinic anhydride, about 40 to about 90 weight percent of said 5-phenyl-5-methylhexane-1,2,3,4-tetracarboxylic acid dianhydride, and about 5 to about 50 weight percent of said addition products; and wherein said cured solid resin has a total anhydride equivalent ratio of about 0.95 to about 1.50 and an amount of said accelerator ranging from about 0.1 to about 8.0 parts per hundred parts resin; and said accelerator is selected from the group consisting of tin octanoate, zinc acetylacetonate, and benzyldimethylamine.

15. A new composition according to claim 1 wherein said 1,2-epoxy resin has an epoxide equivalent between about 400 to about 2,500, is a solid at room temperature (20°–25° C.) and has a Durran melting point between about 50° and 150° C.; said residue consists essentially of about 5 to about 15 weight percent of said dimethylbenzyl succinic anhydride, about 50 to about 80 weight percent of said 5-phenyl-5-methylhexane-1,2,3,4-tetracarboxylic acid dianhydride, and about 10 to about 40 weight percent of said addition products; and wherein said cured solid resin has a total anhydride equivalent ratio of about 1.0 to about 1.40 parts per hundred parts of resin and said accelerator is tin octanoate.

* * * * *